(12) United States Patent
Testa et al.

(10) Patent No.: US 7,211,661 B2
(45) Date of Patent: May 1, 2007

(54) TRANS-EXCISION-SPLICING RIBOZYME AND METHODS OF USE

(75) Inventors: Stephen M. Testa, Lexington, KY (US); Michael A. Bell, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 52 days.

(21) Appl. No.: 10/730,261

(22) Filed: Dec. 9, 2003

(65) Prior Publication Data

US 2004/0219571 A1    Nov. 4, 2004

Related U.S. Application Data

(60) Provisional application No. 60/431,965, filed on Dec. 10, 2002.

(51) Int. Cl.
C07H 21/04     (2006.01)
C12N 15/00     (2006.01)
C12Q 1/68      (2006.01)

(52) U.S. Cl. .................. 536/24.5; 435/320.1; 435/6

(58) Field of Classification Search ............. None
See application file for complete search history.

(56) References Cited

OTHER PUBLICATIONS

Sargueil et al. Journal of Molecular Biology 1993, vol. 233, pp. 629-643.*
Sullenger et al. Nature 1994, vol. 371, pp. 619-622.*
Harley et al. Am. J. Hum. Genet. 1993, vol. 52, pp. 1164-1174.*
Testa et al. Biochemistry 1997, vol. 36, pp. 15303-15314.*
Stephen M. Testa et al., "In Vitro Suicide Inhibition of Self-Splicing of a Group I Intron from Pneumocystis carinii by an N3'-P5' Phosphoramidate Hexanucleotide", Proc. National Academy of Sciences USA, vol. 96, pp. 2734-2739, Mar. 1990, Biochemistry.
Stephen N. Testa et al., "A Pneumocystis carinii Group I Intron Ribozyme that does not Require 2' OH Groups on its 5' Exon Mimic for Binding to the Catalytic Core", Biochemistry 1997, vol. 36, pp. 15303-15314, American Chemical Society 1997.
Arthur J. Zaug et al., "The Intervening Sequence RNA of Tetrahymena is an Enzyme", Science, vol. 231, 1986, pp. 470-475.
Felicia L. Murphy et al., "Alteration of Substrate Specificity for the Endoribonucleolytic Cleavage of RNA by the Tetrahymena Ribozyme", Proc. National Academy of Sciences USA, vol. 86, pp. 9218-9222, Dec. 1989, Biochemistry.
Michael D. Been et al. "One Binding Site Determines Sequence of Tetrahymena Pre-rRNA Self-Splicing, Trans-Splicing, and RNA Enzyme Activity", Cell, vol. 47, pp. 207-216, Oct. 24, 1986, Copyright 1986 by Cell Press.
Arthur J. Zaug et al., "The Tetrahymena Ribozyme Acts Like and RNA Restriction Endonuclease", Nature vol. 324, Dec. 4, 1986, pp. 429-433.
Bruce A Sullenger et al., "Ribozyme-Mediated Repair of Defective mRNA by Targeted Trans-Splicing", Nature vol. 371, Oct. 13, 1994, pp. 619-622.

Ning Lan et al., "Ribozyme-Mediated Repair of Sickle B-Globin mRNAs in Erythrocyte Precursors", Science, vol. 280, Jun. 5, 1998, pp. 1593-1596.
Richard P. Bowater et al., "The Intrinsically Unstable Life of DNA Triplet Repeats Associated with Human Hereditary Disorders", Progress in Nucleic Acid Research and Molecular Biology, vol. 66, pp. 159-202, Copyright 2001 by Academic Press.
Tan Inoue et al., "Intermolecular Exon Ligation of the rRNA Precursor of Tetrahymena: Oligonucleotides Can Function as 5' Exons", Cell, vol. 43, pp. 431-437, Dec. 1985 (Part 1), Copyright 1985 by MIT.
Thomas R. Cech et al., "RNA Catalysis by a Group I Ribozyme", Developing a Model for Transition State Stabilization, The Journal of Biological Chemistry, vol. 267, No. 25, Sep. 1992, pp. 17479-17482.
T. R. Cech et al., "Group I Ribozymes: Substrate Recognition, Catalytic Strategies, and Comparative Mechanistic Analysis", Nucleic Acids and Molecular Biology, vol. 10, pp. 1-17, 1996.
Stephen M. Testa et al., "Antisense Binding Enhanced by Tertiary Interactions: Binding of Phosphorothioate and N3'-P5' Phosphoramidate Hexanucleotides to the Catalytic Core of a Group I Ribozyme from the Mammalian Pathogen Pneumocystis carinii", Biochemistry 1998, vol. 37, pp. 9379-9385.
Mani Mahadevan et al., "Myotonic Dystrophy Mutation: An Unstable CTG Repeat in the 3' Untranslated Region of the Gene", Reports, Mar. 6, 1992, pp. 1253-1255.
Helen G. Harley et al., "Size of the Unstable CTG Repeat Sequence in Relation to Phenotype and Parental Transmission in Myotonic Dystrophy", American Journal of Human Genetics, vol. 52, pp. 1164-1174, 1993.
Matthew D. Disney et al., "Contributions of Individual Nucleotides to Tertiary Binding of Substrate by a Pneumocystis carinii Group I Inton", Biochemistry 2000, vol. 39, pp. 14269-14278.
Stephen M. Testa et al., "Thermodynamics of RNA—RNA Duplexes with 2- or 4- Thiouridines: Implications for Antisense Design and Targeting a Group I Intron", Biochemistry 1999, vol. 38, pp. 16655-16662.
Yong Liu et al., "Bidirectional Effectors of a Group I Intron Ribozyme from Pneumocystis carinii", Workshops on Opportunistic Protists, pp. 101S.

* cited by examiner

Primary Examiner—James Schultz
Assistant Examiner—Tracy Vivlemore
(74) Attorney, Agent, or Firm—McDermott Will & Emery LLP

(57) ABSTRACT

A group I intron-derived ribozyme which binds RNA in trans, excises an internal segment from within the RNA, and splices the remaining 5' and 3' ends of the RNA back together (the trans-excision-splicing reaction) is disclosed. The excised segment can be as long as 28 nucleotides, or more, and as little as one nucleotide. The ribozymes of the invention are easily modified to alter their sequence specificity. Such ribozymes represent a new and potentially powerful class of generally adaptable genetic therapeutics.

8 Claims, 8 Drawing Sheets

FIG. 2B(iii)

FIG. 2B(ii)

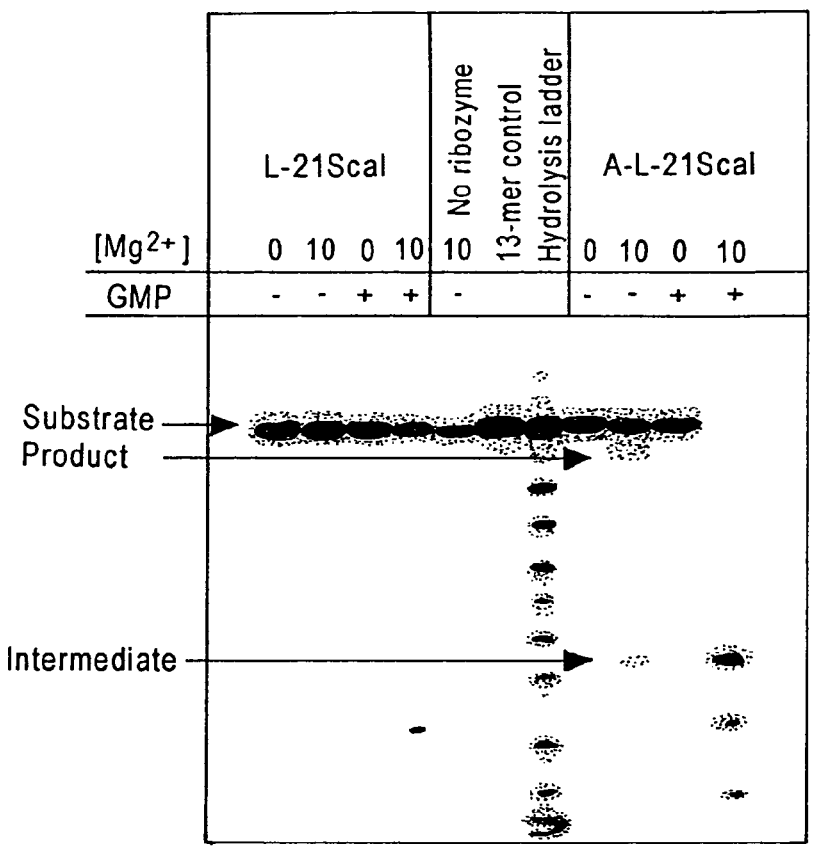
FIG. 7A
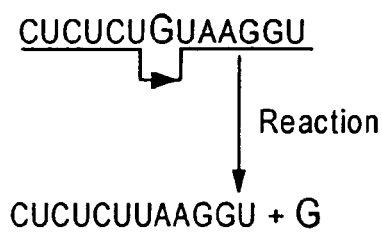
FIG. 7B
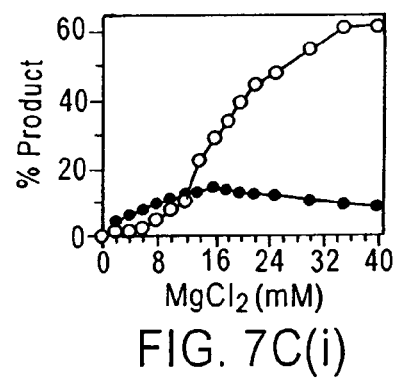
FIG. 7C(i)
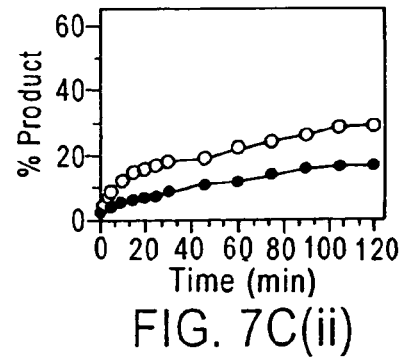
FIG. 7C(ii)

TRANS-EXCISION-SPLICING RIBOZYME AND METHODS OF USE

This application claims priority to Provisional Application Ser. No. 60/431,965, filed Dec. 10, 2002.

FIELD OF THE INVENTION

This invention relates generally to the field of genetic therapeutics. More particularly, the invention relates to a trans-excision-splicing ribozyme having adaptable sequence recognition specificity that provides a powerful tool for genetic therapies.

BACKGROUND OF THE INVENTION

The discovery of catalytic RNA fundamentally changed the course of science. The subsequent realization that catalytic RNAs could be tailored to suit individual needs has been nothing less than inspiring. Indeed, the past ten years has seen the creative development of numerous RNA catalysts. Concurrently, the diversity of applications for these catalytic RNAs has been escalating. For example, catalytic RNAs are being developed for detection protocols, for therapeutic intervention of diseases, and for use as biochemical tools. As we continue to exploit the steadily increasing knowledge base of RNA structure, folding, and catalysis, designing and applying novel and effective RNA catalysts is becoming more and more tractable.

Ribozymes are RNA molecules having an enzymatic activity, which enables the ribozyme to repeatedly cleave other separate RNA molecules in a nucleotide base sequence-specific manner. Such enzymatic RNA molecules can be targeted to virtually any RNA transcript, and efficient cleavage achieved in vitro. Kim et al., 84 Proc. Natl. Acad. Sci. USA 8788, 1987; Haseloff and Gerlach, 334 Nature 585, 1988; Cech, 260 JAMA 3030, 1988; and Jefferies et al., 17 Nucleic Acids Research 1371, 1989.

Ribozymes act by first binding to a target RNA. Such binding occurs through the target RNA binding portion of a ribozyme, which is held in close proximity to an enzymatic portion of the RNA that acts to cleave the target RNA. Thus, the ribozyme first recognizes and then binds a target RNA through complementary base-pairing, and once bound to the correct site, acts enzymatically to cut the target RNA. Strategic cleavage of such a target RNA destroys its ability to direct synthesis of an encoded protein. After a ribozyme has bound and cleaved its RNA target it is released from that RNA to search for another target and can repeatedly bind and cleave new targets.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

A catalytic RNA that can excise a specific RNA sequence out of a larger RNA (the trans-excision-splicing reaction), although not previously discovered or engineered, would be very useful as a biochemical tool and also as a potential new therapeutic strategy. For example, multiple turnover catalytic RNAs, or ribozymes, with this activity could be used to excise a disease-causing RNA region out of a native transcript, to remove a premature stop codon, or to restore a frameshift mutation, for example.

SUMMARY OF THE INVENTION

In one aspect of the invention there is provided a trans-excision-splicing ribozyme comprising at least two recognition elements that are complementary to a target sequence within a substrate, wherein the target sequence is not complementary to native recognition elements, wherein at least one of said recognition elements stabilizes binding of the ribozyme to a trans-excision splicing (TES) reaction intermediate product, and wherein the ribozyme catalyzes a specific excision of the target sequence and splices the 5' end of the substrate created by the excision to an ωG of the 3' end of the substrate created by the excision.

In another aspect of the invention there is provided a polynucleotide molecule comprising a ribozyme expression cassette that is capable of being stably inserted into a host, the cassette comprising a promoter operably-linked to a nucleotide sequence encoding a trans-excision-splicing ribozyme comprising at least two recognition elements that are complementary to target sequence within a substrate other than that complementary to native recognition elements, wherein at least one of said recognition elements stabilizes binding of the ribozyme to a trans-excision splicing (TES) reaction intermediate product and wherein the ribozyme catalyzes a specific excision of the target sequence and splices the 5' end of the substrate created by the excision to an ωG of the 3' end of the substrate created by the excision.

Also provided are host cells transfected with the polynucleotide molecule.

In yet another aspect of the invention there is provided a method for in vitro trans-splicing-excison of a target sequence, comprising the steps of:

(1) providing the ribozyme of the invention in a trans-splicing reaction mixture;

(2) providing a substrate comprising the target sequence to the reaction mixture; and (3) catalyzing the trans-splicing-excision of the target sequence.

In another aspect of the invention there is provided a method for deleting an undesired genetic sequence from a host cell in vivo, said method comprising:

(1) providing the ribozyme of the invention to the host cell, said ribozyme possessing catalytic activity against a target RNA sequence present in said host cell, wherein the ribozyme catalyzes a specific excision of the target RNA sequence and splices the 5' end of the substrate created by the excision to an ωG of the 3' end of the substrate created by the excision.

The following definitions are used herein.

Ribozyme: An RNA molecule that inherently possesses catalytic activity.

Trans-splice: A form of genetic manipulation whereby a nucleic acid sequence of a first polynucleotide is colinearly linked to or inserted colinearly into the sequence of a second polynucleotide, in a manner that retains the 3'-5' phosphodiester linkage between such polynucleotides. By "directed" trans-splicing or "substrate-specific" trans-splicing is meant a trans-splicing reaction that requires a specific specie of RNA as a substrate for the trans-splicing reaction (that is, a specific specie of RNA in which to splice the transposed sequence). Directed trans-splicing may target more than one RNA specie if the ribozyme is designed to be directed against a target sequence present in a related set of RNAs.

Target sequence: A nucleic acid molecule, e.g., RNA, that is a substrate for the catalytic activity of a ribozyme of the invention.

Expression Cassette: A genetic sequence that provides sequences necessary for the expression of a ribozyme of the invention.

Stably: By "stably" inserting a sequence into a genome is intended insertion in a manner that results in inheritance of such sequence in copies of such genome.

Operable linkage: An "operable linkage" is a linkage in which a sequence is connected to another sequence (or sequences) in such a way as to be capable of altering the functioning of the sequence (or sequences). For example, by operably linking a ribozyme encoding sequence to a promoter, expression of the ribozyme encoding sequence is placed under the influence or control of that promoter. Two nucleic acid sequences, such as a ribozyme encoding sequence and a promoter region sequence at the 5' end of the encoding sequence, are said to be operably linked if induction of promoter function results in the transcription of the ribozyme encoding sequence and if the nature of the linkage between the two sequences does not (1) result in the introduction of a frame-shift mutation, (2) interfere with the ability of the expression regulatory sequences to direct the expression of the ribozyme. Thus, a promoter region would be operably linked to a nucleic acid sequence if the promoter were capable of effecting the synthesis of that nucleic acid sequence.

Native target sequence/Non-native target sequence: Native target sequence of a ribozyme is that polynucleotide sequence which is recognized, bound and reacted by wild-type (native) ribozymes. Non-native target sequence is sequence within a substrate that is not bound by wild type ribozyme and consequently native ribozyme does not react with non-native target sequence. Non-native target sequence can occur as a result of mutation, for example.

BRIEF DESCRIPTION OF THE DRAWINGS

FIG. 7. TES reactions using two different Tetrahymena ribozymes. FIG. 7A is a polyacrylamide gel showing substrates, intermediates, and products of the TES reaction. The reaction was carried out for 90 minutes using 166 nM ribozyme and 1.33 nM radiolabeled 13-mer substrate at either 0 mM or 10 mM MgCl$_2$ at 44 degrees C, either in the presence (+) or absence (−) of 330 nM GMP. FIG. B is a diagram of the TES reaction (SEQ ID NO:19 and SEQ ID NO:20). The excised G of SEQ ID NO:19 is in bold lettering. FIG. 7C shows two graphs of TES reactions using the 13-mer substrate and the A-L-21 Sca ribozyme (*Tetrahymena*). The TES product is represented by the filled circles and the 5' intermediate (CUCUCU) (SEQ ID NO:21) is represented by open circles. All reactions were run as above except for the changing variable. Each curve represents the average of two independent assays. Standard deviation for all points was less than 10%. For clarity the graphs use different scales.

DETAILED DESCRIPTION OF THE INVENTION

Figure 1A:
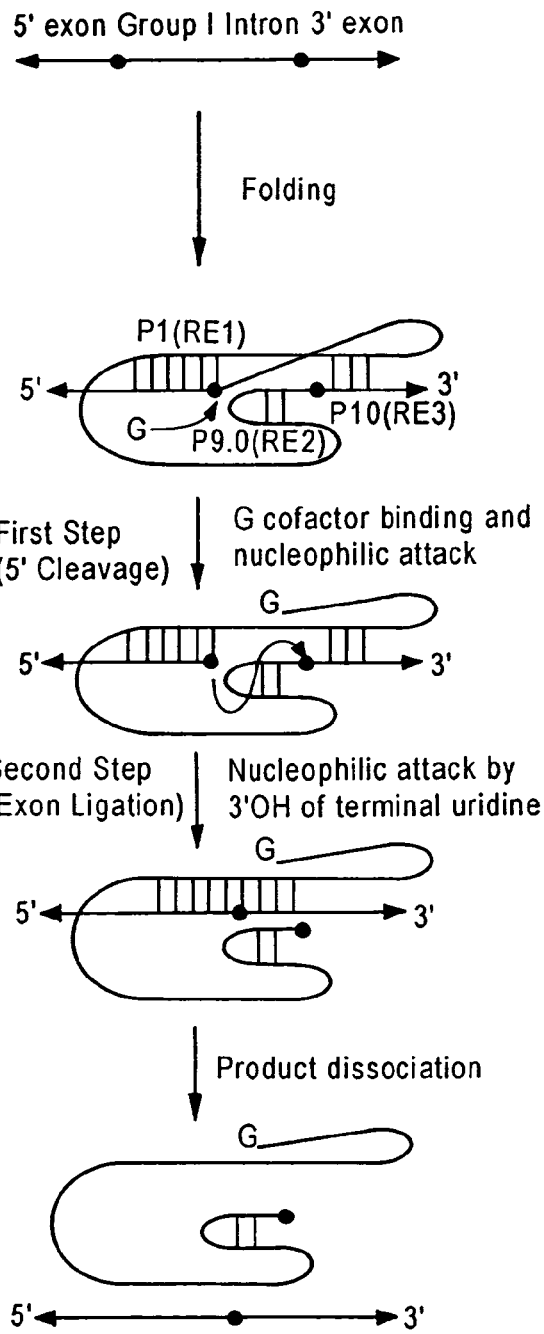
FIG. 1. The Group I Intron Self-Splicing (1a: left) and Trans-Excision-Splicing Reactions (1b: right). The catalytic RNAs are represented by gray lines, the 5' and 3' exons and mimics are black lines, and the bridge (excised region) is a dotted line. The circle in the 5' exon represents a uridine and the circle in the 3' exon represents a guanosine. The intron inherently contains all the required activities for the trans-excision-splicing reaction. RE1, RE2, and RE3 are three recognition elements that the catalytic RNAs may use to base pair with their substrates (RE1 is also referred to as the IGS, or Internal Guide Sequence.). It is likely that RE2 and/or RE3 do not bind the substrate until after the first reaction step. In addition, at least with the rP-8/4x ribozyme used herein, the guanosine cofactor is not required for initiation of the first catalytic step.
Figure 1B:
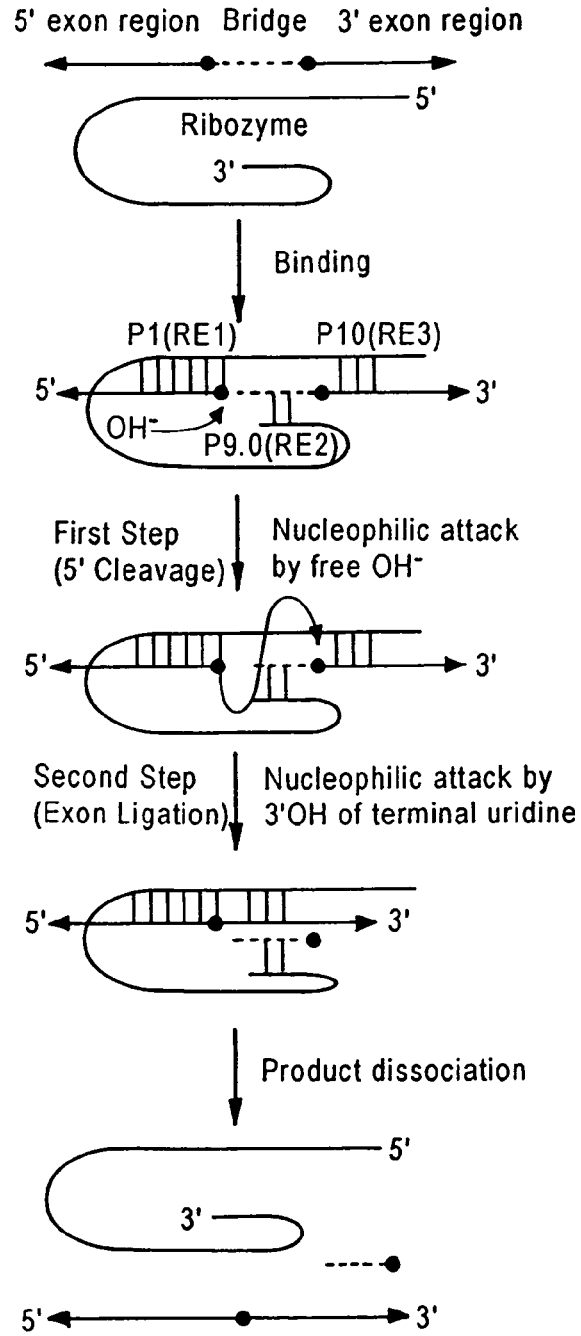
Figure 2A:
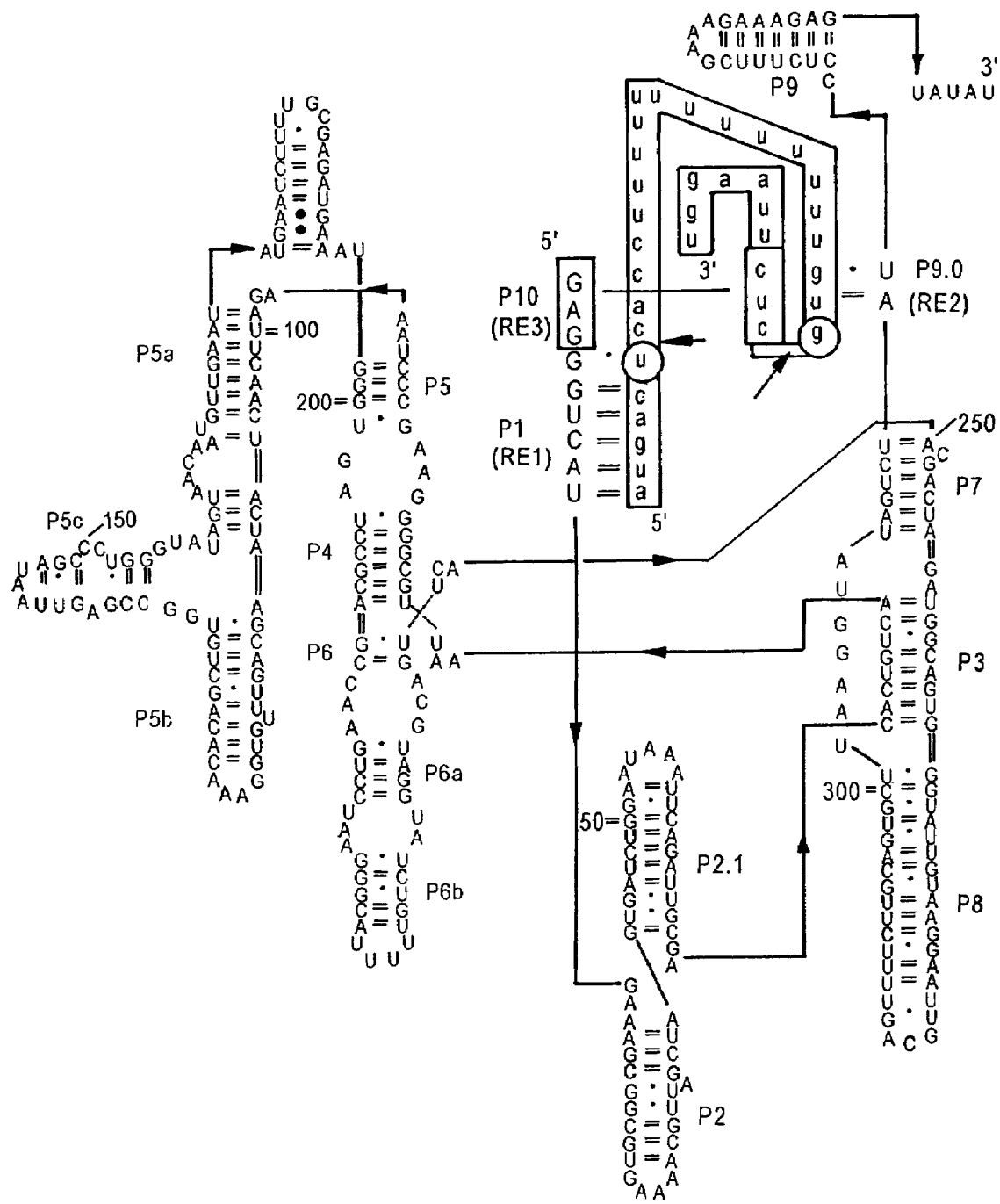
FIG. 2. The rP-8/4x and rP-8/4x-MD Ribozymes Base Pairing with Various Substrates. 2A) The P. carinii ribozyme, rP-8/4x (uppercase lettering. SEQ ID NO:9), binding to the 36-mer substrate (lowercase lettering with a gray background, SEQ ID NO:10). In the trans-excision-splicing reaction, the bridging region (white lettering) is excised and the 5' and 3' regions of the substrate (black lettering) are subsequently spliced together. Note that P1, P9.0, and P10 are helices that result from the recognition elements RE1, RE2, and RE3 base pairing with the substrate. The large bold arrows indicate the sites of catalysis for the first (left) and second (right) step of the trans-excision-splicing reaction. The 5' uridine and 3' guanosine are circled. The ribozyme bases are numbered according to that for the P. carinii intron (Testa, S. M., Haidaris, C. G., Gigliotti, F., & Turner, D. H. (1997) Biochemistry 36, 15303–153 14.13, incorporated herein in its entirety). 2B). Simplified diagrams of various substrates base pairing with various ribozymes. Only the recognition element sequences are shown for the ribozymes. The dashed line indicates a normal phosphodiester bond between the adjoining sequences. i) The 12-mer substrate (SEQ ID NO:7) binding to rP-8/4x (SEQ ID NO:11). ii) The 10-mer substrate (SEQ ID NO:8) binding to rP-8/4x (SEQ ID NO:11). iii) The 38-mer Myotonic Dystrophy substrate (SEQ ID NO: 12) binding to the rP8/4x-MD Myotonic Dystrophy ribozyme (SEQ ID NO:13).

The inherent binding and catalytic activity of group I intron-derived ribozymes can be exploited to catalyze the trans-excision-splicing reaction. FIG. 1*a* shows a simple diagram of a typical group I intron-catalyzed self-splicing reaction. There are three base pairing contacts that the intron uses to hold and position its 5' and 3' exons for subsequent catalysis. We have termed these the ribozyme recognition elements, or RE1, RE2, and RE3. Physically removing the intramolecular exons from the intron creates a ribozyme that has the ability to bind and catalyze reactions using exogenous substrates that contain 5' and 3' exon sequences (Zaug, A. J. & Cech, T. R. (1986) Science 231, 470–475.). If the 5' and 3' exon sequences are connected with a bridging sequence and recognition elements are maintained, this ribozyme can excise the bridging sequence and splice the 5' and 3' ends of the substrate together. A simple diagram of this trans-excision-splicing reaction is shown in FIG. 1*b*. This reaction was tested using a ribozyme, rP-8/4x, from the opportunistic pathogen *Pneumocystis carinii*. In FIG. 2A it is shown that this ribozyme catalyzes the trans-excision-splicing reaction using a synthetic substrate which is complementary to the native recognition elements of the rP-8/4x ribozyme. Moreover, as little as a single nucleotide can be excised.

In order for this reaction to be useful, however, the ribozyme recognition elements have to be mutable, such that the ribozyme can be targeted to bind with and react on non-native sequences. Using a group I intron-derived ribozyme from *Tetrahymena thermophila*, the sequence of RE1 (also referred to as the IGS, or Internal Guide Sequence) was mutated and the resultant ribozyme then bound to a new, complementary substrate (Murphy, F. L. & Cech, T. R. (1989) *Proc. Natl. Acad. Sci. U.S.A.* 86, 9218–9222; Been, M. D. & Cech, T. R. (1986) *Cell* 47, 207–216; Zaug, A. J., Been, M. D., & Cech, T. R. (1986) *Nature* 324, 429–433). This property has been exploited for, among other purposes, designing trans-splicing ribozymes that can replace the 3' end of mutant transcripts with corrected versions (Sullenger, B. A. & Cech, T. R. (1994) *Nature* 371, 619–6; Lan, N., Howrey, R. P., Lee, S. W., Smith, C. A., & Sullenger, B. A. (1998) *Science* 280, 1593–1596).

Trans-excision-splicing ribozymes are ideal for treating genetic diseases for which the causative affects may be ameliorated by the excision of an internal RNA segment out of a larger RNA, including triplet-expansion diseases such as Huntington's disease, Fragile X, and Myotonic Dystrophy (Bowater, R. P. & Wells, R. D. (2001) Prog. Nucleic Acid Res. Mol. Biol. 66, 159–202). Patients affected with these diseases have an RNA that is present in normal individuals, except that embedded within it is an abnormally high number of tandem repeat sequences. For Myotonic Dystrophy, the expansion is in the 3' UnTranslated Region [3' UTR] of a serine-threonine protein kinase gene [the DMPK gene], whose expression induces the expression of skeletal muscle specific genes. The disease state of Myotonic Dystrophy, which is the most common form of adult onset Muscular Dystrophy, typically has much more than 35 CUG repeats, while unaffected individuals typically have less than 15 repeats. The greater the number of repeats, the more severe the affects of the disease. Moreover, strong experimental evidence indicates the disease stems directly from the RNA repeats, and not to any affected coding potential of the parent DNA. In fact, the Myotonic Dystrophy triplet-expansion and recently discovered quadruplet-expansion diseases have the repeat sequences within non-coding regions, so their effects are not due to the synthesis of mutant proteins. A new class of ribozymes that can specifically excise these expanded RNA repeats from the transcripts could aid in the development of much needed therapeutics against these types of diseases.

The rP-8/4x ribozyme was re-engineered to test the potential to alter the sequence specificity of trans-excision-splicing ribozymes to bind and excise the triplet expansion region from a Myotonic Dystrophy DMPK small model system in vitro. The resultant ribozyme excises the triplet expansion region, and in a sequence specific manner. That trans-excision-splicing ribozymes can be re-engineered to target and act upon predetermined sequences demonstrates a general usefulness for these ribozymes as biochemical tools and therapeutics.

*P. carinii* group I intron ribozyme catalyzes the trans-excision-splicing reaction.

A ribozyme derived from a *P. carinii* group I intron catalyzes a previously unreported excision-splicing reaction on an exogenous substrate. This trans-excision-splicing reaction takes advantage of the catalytic abilities of this ribozyme. First, rapid and efficient sequence-specific cleavage of a designated substrate occurs in a guanosine independent fashion, as previously reported (Testa, S. M., Haidaris, C. G., Gigliotti, F., & Turner, D. H. (1997) Biochemistry 36, 15303–15314.). Second, the resultant 5' cleavage product can splice to a sequence that binds the 3' end of the ribozyme (Inoue, T., Sullivan, F. X., & Cech, T. R. (1985) Cell 43, 431–437) (FIG. 1B). These activities were exploited by designing a synthetic substrate that contains within it the sequences required for each catalytic event, separated by an internal bridging sequence (FIG. 2A). As seen in FIG. 3, the engineered ribozyme catalyzes the specific excision of the bridge sequence and splices the 5' and 3' ends of the substrate back together. Even though there are 18 other uridines that could be sites of 5' cleavage and 4 other guanines that could be sites of 3' splicing, only one trans-excision-splicing product is generated. Apparently, the ribozyme recognition elements that define the individual catalytic steps are sequence specific.

That the ribozyme can catalyze this reaction is surprising in that the relatively long bridging region could be expected to sterically hinder the binding of the substrate to the catalytic core of the ribozyme or hinder the required conformational rearrangement between the two catalytic steps (Cech, T. R., Herschlag, D., Piccirilli, J. A., & Pyle, A. M. (1992) J. Biol. Chem. 267, 17479–17482; and 39. Jaeger, L., Michel, F. & Westhof, E. (1996) in Catalytic RNA, eds. Eckstein, F. & Lilley, D. (Heidelberg, Germany), Vol. 10, pp. 1–17). Perhaps this accounts for over 50% of the substrate only undergoing the first catalytic step (see FIG. 3). In addition, like other ribozymes, the *P. carinii* ribozyme binds its 5' exon sequences orders of magnitude tighter than its 3' exon sequences, which allows time for 3' end dissociation prior to the second catalytic step. Nevertheless, a significant amount of trans-excision-splicing product is generated. Another consideration is that the 5' exon of one substrate could ligate to the 3' exon of another substrate. Since spontaneous 3' splice site hydrolysis is essentially non-existent and only an insignificant amount of 5' exon-bridge 26-mer product (which would be a side reaction of this catalytic event) is produced, it is unlikely that this mechanism occurs to a significant extent.

The *P. carinii* ribozyme can excise as little as one nucleotide. The *P. carinii* ribozyme excises as little as a single nucleotide, and in a sequence-specific manner. Apparently, there is no lower limit to the size of the region being excised. That the same approximate yield is obtained regardless of whether the 12-mer (39%) and 10-mer (36%) substrate is used suggests that the role of forming the P9.0 helix is not large in this case, as the 10-mer lacks the ability to form the P9.0 helix. Therefore, the RE2 interaction, although perhaps beneficial, is not required to establish a sequence specific interaction. In addition, the 12-mer and 10-mer substrates lead to approximately 50% more product as compared with the 36-mer substrate. There are many possible explanations for this, including the longer bridge of the 36-mer substrate partially interfering with the substrate's ability to bind the recognition elements.

The sequence specificity of the *P. carinii* ribozyme can be altered. Altering the recognition elements of the *P. carinii* ribozyme changes the sequence specificity of the trans-excision-splicing reaction. While it was known that RE1 could be modified in reactions mimicking the first step of the self-splicing reaction, it was previously not known that all three elements are mutable. That these recognition elements completely specify binding and reactivity indicates that they are the primary determinants of specificity between the ribozyme and its substrate. In addition, bridging regions of different sequences and lengths (1, 3, 20, and 28 nucleotides) have been excised, indicating that the 3' G in the bridging region might be the only potential sequence requirement for the excised segment. Structure might even be tolerated within the excised region, as the somewhat structured CUG repeat within the Myotonic Dystrophy substrate doesn't prohibit the reaction. In addition, each ribozyme only acts upon its designated target, even though the RE1s in both ribozymes are 50% identical, giving a further indication of the high level of sequence specificity of this reaction. Although the $MgCl_2$ concentration required for maximum activity is different for the two ribozymes (7 and 13 mM), they both are active throughout the same general $MgCl_2$ concentration range (data not shown), which is below that required (15 mM) for maximum activity for the *P. carinii* group I intron self-splicing reaction in vitro.

The ability to catalyze TES reactions is inherent to Group I introns. To determine whether other ribozymes can catalyze TES reaction, a *Tetrahymena* —containing L-21 ScaI plasmid was linearized with ScaI, run-off transcriptions were performed, and the ribozyme was purified as described by Testa et al. (Biochemistry, (1997) 36:15303–15314). TES reactions were run in a variety of standard buffers and conditions routinely used for ribozyme reactions. The reactions were also run in the presence and absence of the PG cofactor. In all cases, the first step of the reaction was the only reaction step that was detected.

The lack of a full-length, second-step reaction product suggests that the second step may be inefficient or problematic with this ribozyme. Our previous studies of the *P. carinii* ribozyme had demonstrated that 3' intermediate disassociation results in significantly reduced second-step yields. Therefore, the *Tetrahymena* ribozyme was modified to contain an RE3 region in order to stabilize binding of the ribozyme to the '3 exon reaction intermediate. The results are shown in FIG. 6. The reaction using the stabilized ribozyme generates a product band of the expected size (a 12-mer product from a 13-mer substrate). The product band was excised from the band and sequenced, and shown to be the expected TES product. These results demonstrate that the the ability to catalyze TES reactions is a general property inherent to group I introns.

Comparison with the Trans-Splicing Reaction. The trans-excision-splicing reaction of the invention is fundamentally different from the trans-splicing reaction previously reported (Sullenger, B. A. & Cech, T. R. (1994) Nature 371, 619–622.), whereby a ribozyme covalently attached to a normal RNA sequence binds to a mutant RNA transcript, cleaves the mutant transcript, and replaces the 3' end of the mutant transcript with the normal 'corrected' version. While trans-splicing can correct mutant RNA, it is single-turnover, it exploits only the RE1 molecular interaction, and the ribozyme must be covalently attached to the new, corrected transcript. In contrast, the trans-excision-splicing reaction is potentially multiple turnover; it exploits the RE1, RE2, and/or RE3 molecular interactions; and it excises an internal segment from within a larger RNA. Nevertheless, these two complementary reactions share many similarities and so the wealth of knowledge already reported for the trans-splicing reaction is applicable to the trans-excision-splicing reaction.

Implications for Myotonic Dystrophy. The rP-8/4x ribozyme can be redesigned to specifically excise the entire triplet expansion region of a mimic of the Myotonic Dystrophy transcript, implicating such ribozymes as new types of potential Muscular Dystrophy therapeutics. As a practical matter, cutting out this entire region may or may not restore proper function to the transcript, as normal individuals typically have at least 5 repeats. Similar multiple turnover ribozymes, however, can be designed to target the repeats themselves to successively reduce expansion lengths.

General Therapeutic Implications. Unfortunately, nature has afforded a huge number of RNA-mediated mutations that predispose individuals to disease. New therapeutic strategies to combat these diseases are needed. That the recognition elements of the rP-8/4x ribozyme can be modified and the size and sequence of the excised region do not appear to have limitations suggest that trans-excision-splicing ribozymes may be generally useful as therapeutics against many such diseases. For example, excising specific sequences could remove premature stop codons, restore altered reading frames, or remove insertion mutations that affect transcription and translation regulation.

Trans-excision-splicing ribozymes are thought to have two sequence preferences. The first is a uridine at the 5' cleavage site (although a cytidine might also work) and the second is a guanosine at the 3' splice site (FIG. 2A). Therefore, there are three simple targeting strategies to consider. First, a ribozyme can be designed that targets a uridine 5' to any particular mutation and a guanosine 3' to this mutation, as is the case in the Myotonic Dystrophy model system described here. It should be noted that if more than an insertion mutation is excised the new transcript might not function normally. Second, a mutation that results in a new guanosine can be targeted as the 3' splice site. The above strategies will also target normal transcripts for at least the first step of the reaction, so these strategies should be designed with care. Third, a mutation that results in a new uridine can be targeted as the 5' cleavage site. This resultant ribozyme would not attack the normal transcript, but would perform both steps on the mutant transcript. Since point mutations that result in premature termination codons often involve a new uridine (all termination codons begin with uridine), hundreds of distinct mutations could be specifically targeted. Therefore, many options for targeting are possible, which expands the potential usefulness of these ribozymes. The general strategy of targeting mutations at the RNA level, however, should be considered a potential treatment rather than a potential cure, as mutant RNA transcripts will continue to be produced.

As shown herein, group I intron-derived ribozymes obtained from different organisms can catalyze this new trans-excision-splicing reaction. In addition, the sequence of the ribozyme can be easily manipulated such that it targets and acts upon desired substrates, including those of medical importance. The reactions themselves appear highly sequence specific and as little as a single nucleotide can be excised. The applicability of trans-excision-splicing ribozymes to treat disease has been demonstrated by designing a ribozyme that specifically removes the triplet expansion region that is involved in a common form of Muscular Dystrophy in a small model system in vitro. Therefore, trans-excision-splicing ribozymes are a new class of ribozymes that permits potential biochemical and therapeutic strategies not before possible.

The ribozymes of the invention can be introduced into and expressed in a host cell. Transcription of the ribozyme of the invention in a host cell occurs after introduction of the ribozyme gene into the host cell. If the stable retention of the ribozyme by the host cell is not desired, the ribozyme may be chemically or enzymatically synthesized and provided to the host cell by mechanical methods, such as microinjection, liposome-mediated transfection, electroporation, calcium phosphate precipitation, or the like. Alternatively, when stable retention of the gene encoding the ribozyme is desired, such retention may be achieved by stably inserting at least one DNA copy of the ribozyme into the host's chromosome, or by providing a DNA copy of the ribozyme on a plasmid that is stably retained by the host cell. Preferably the ribozyme of the invention is inserted into the host's chromosome as part of an expression cassette, which provides transcriptional regulatory elements that control the transcription of the ribozyme in the host cell. Such elements may include, but not necessarily be limited to, a promoter element, an enhancer or UAS element, and a transcriptional terminator signal. Polyadenylation is not necessary as the ribozyme is not translated.

Expression of a ribozyme whose coding sequence has been stably inserted into a host's chromosome is controlled by the promoter sequence that is operably linked to the ribozyme coding sequences. The promoter that directs expression of the ribozyme may be any promoter functional in the host cell, prokaryotic promoters being desired in prokaryotic cells and eukaryotic promoters in eukaryotic cells. A promoter is composed of discrete modules that direct the transcriptional activation and/or repression of the promoter in the host cell. Such modules may be mixed and matched in the ribozyme's promoter so as to provide for the proper expression of the ribozyme in the host. A eukaryotic promoter may be any promoter functional in eukaryotic cells, and especially may be any of an RNA polymerase I, II or III specificity. If it is desired to express the ribozyme in a wide variety of eukaryotic host cells, a promoter functional in most eukaryotic host cells should be selected, such as a rRNA or a tRNA promoter, or the promoter for a widely expressed mRNA such as the promoter for an actin gene, or a glycolytic gene. If it is desired to express the ribozyme only in a certain cell or tissue type, a cell-specific (or tissue-specific) promoter element that is functional only in that cell or tissue type should be selected.

The trans-splicing reaction is chemically the same whether it is performed in vitro or in vivo. However, in vivo, the presence of the target and the ribozyme will suffice to result in trans-splicing, since cofactors are usually already present in the host cell.

It has been previously reported that, at high $MgCl_2$ (10–100 mM) and temperature (55° C. to 65° C.), *Tetrahymena* group I intron ribozymes that lack both of the exons and the IGS can catalyze a guanosine cofactor-mediated TES-like reaction upon binding pseudoknot structured substrates, which creates the in trans equivalent of the P1 and P10 helices (P9.0 helix formation was not required). The ribozymes target and bind these pseudoknot structures entirely through tertiary interactions. In contrast, the ribozymes used in the present invention contain at least two modifiable REs. In a preferred embodiment, the ribozyme conatins modified RE1 and RE3. which allows the ribozyme to target designated substrates at the level of simple base pairing. Furthermore, the TES reactions using the *P. carinii* and *Tetrahymena* ribozymes do not require a guanosine cofactor, and optimally occur at a lower $MgCl_2$ concentration (7–13 mM) and temperature (44° C.).

Sullenger and Cech ((1994) *Nature* 371, 619–622.) previously reported that *Tetrahymena* group I intron ribozymes that lack a 5' exon, but contain an endogenous non-native 3' exon, catalyze the covalent attachment of the endogenous 3' exon to mutant transcripts in such a way as to replace the 3' end of mutant transcripts with normal 'corrected' versions. While trans-splicing can repair RNA, it exploits only the RE1 molecular interaction, the ribozymes must be covalently attached to the repaired half of the transcript, it is single-turnover, and repairing mutations distant from the 3' end of long transcripts could be problematic. In contrast, the TES reaction exploits multiple molecular interactions (RE1, RE3, and perhaps RE2), TES ribozymes excise an internal segment from within RNA substrates, the reaction is potentially multiple turnover, and the position of the mutations within the transcript is not a limiting factor. Moreover, that under the conditions used in this report, little (if any) turnover was observed.

EXAMPLE 1

Oligonucleotide synthesis and preparation. DNA oligonucleotide primers were purchased from Integrated DNA Technologies (Coralville, Iowa), and were used without further purification. RNA oligonucleotides were purchased from Dharmacon Research Inc. (Boulder, Colo.) and deprotected following the manufacturer's protocol. The oligoribonucleotides were 5' end radiolabeled and purified via gel electrophoresis as previously described (Testa, S. M., Haidaris, C. G., Gigliotti, F., & Turner, D. H. (1997) *Biochemistry* 36, 15303–15314.). The RNA products were extracted from the gel slice by stirring for one hour with a sterile stir-bar in 1.5 mL elution buffer containing 10 mM Tris (pH 7.4), 250 mM NaCl, and 1 mM EDTA. Gel particulate was removed via centrifugation, and the solution was evaporated to a final oligoribonucleotide concentration of approximately 8 nM.

Plasmid construction and synthesis. The *P. carinii* ribozyme plasmid precursor, P-8/4x, was generated as previously described (Testa, S. M., Haidaris, C. G., Gigliotti, F., & Turner, D. H. (1997) *Biochemistry* 36, 15303–153 14). The Myotonic Dystrophy-specific ribozyme plasmid precursor, P-8/4x-MD, was derived from the P-8!4x plasmid by site-directed mutagenesis. Briefly, three successive rounds of mutagenesis were performed to modify each of the three recognition elements using the following pairs of mutagenic primers (underlined bases represent altered recognition elements as compared to P-8/4x): 5' CACGCCGCTTTC GGGAACCTCTATAGTGAGTCG3' (SEQ ID NO:1) and 5' CGACTCACTATAGAGGTTCCCGAAAGCGGCGTG3' (SEQ ID NO:2) for RE1 formation, 5' GGTATAGTCT TGCCTCTTTCGAAAG3' (SEQ ID NO:3) and 5' CTTTC-GAAAGAGGCAAGACTATACC3' for RE2 (SEQ ID NO:4) formation, and then 5' CGACTCACTATA GGTGTTCCCGAAAGCGGC3' (SEQ ID NO:5) and 5' GCCGCTTTCGGGAACACCTATAGTGAGTCG3' (SEQ ID NO:6) for RE3 formation.

Each set of primers (15 pmol each primer) was used in an amplification reaction comprising 25 ng parental plasmid, 2.5 units Pfu DNA polymerase (Stratagene; La Jolla, Calif.), and 0.5 µM dNTPs in a buffer comprising 10 mM KCl, 10 mM $(NH_4)_2SO_4$, 20 mM Tris-HCl (pH 8.8), 2 mM $MgSO_4$, 0.1% Triton X-100, and 0.1 mg/mL BSA (final volume 50 uL). After an initial denaturation for 30 seconds at 95° C., the mixture was subjected to 15 cycles of 95° C. for 30 seconds, 50° C. for two minutes, and 68° C. for six minutes. Parental plasmid was then digested with 20 units Dpn I (Gibco BRL; Rockville, Md.) in 5.7 µL of the manufacturer's supplied buffer for 2 hours at 37° C. 3 µL of this mixture was then used to transform *E. coli* DH5α competent cells (Gibco BRL). The vectors were purified using a QIAprep Spin Miniprep Kit (QIAGEN; Valencia, Calif.). The resultant final plasmid, P-8/4x-MD, was sequenced for confirmation (ACGT, Inc; Northbrook, Ill.). The plasmids were linearized with Xba I, phenol/chloroform extracted, and ethanol precipitated in preparation for run-off transcription.

Transcription. Both rP-8/4x and rP-8/4x-MD were transcribed from their appropriate plasmid precursors essentially as previously described for rP-8/4x (Testa, S. M., Haidaris, C. G., Gigliotti, F., & Turner, D. H. (1997) *Biochemistry* 36, 15303–15314). A typical transcription reaction (40 µL) contained 1 µg linearized plasmid, 40 mM Tris-HCl (pH 7.4), 5 mM dithiothreitol, 5 mM spermidine, 5 mM $MgCl_2$, 1.5 mM each NTP, 1.25 mg/mL BSA, and 4 µL of T7 RNA polymerase (100 units/µL) and was incubated for two hours at 37° C. The resultant RNA was purified using QIAGEN-tip 100 anion-exchange columns. First, each column was equilibrated with 4.0 mL of Buffer I (750 mM NaCl, 50 mM MOPS (pH 7.0), 15% ethanol, and 0.15% Triton X-100). Second, the transcription reactions were loaded onto the column and the column was washed with 7.0 mL of Buffer I. Third, the transcripts were eluted using 4.0 mL of Buffer II (1.0 M NaCl, 50 mM MOPS (pH 7.0), and 15% ethanol). Following an isopropanol and then an ethanol precipitation, the samples were dissolved in water and quantified using a Beckman UV-VIS DU-650 spectrophotometer.

Trans-excision-splicing reactions. Reactions were conducted in HxMg buffer consisting of 50 mM Hepes (25 mM $Na^+$), 135 mM KCl, and xmM $MgCl_2$ (listed in the figures) at pH 7.5. The trans-excision-splicing reactions were optimized for the rP-8/4x and rP-8/4x-MD ribozymes over a $MgCl_2$ concentration range of 0 to 50 mM at 30° C., 37° C., and 44° C. Maximum product formation occurred at 44° C. for both ribozymes, 7 mM $MgCl_2$ for rP-8/4x, and 13 mM $MgCl_2$ for rP-8/4x-MD, although a significant amount of each product was obtained at 37° C. at both 7 and 13 mM $MgCl_2$ for each ribozyme (data not shown). Prior to each reaction, 1.0 pmol of ribozyme in 5.0 µL of the appropriate buffer was preannealed at 60° C. for five minutes and then allowed to slow-cool to the appropriate temperature. Reactions using the rP-8/4x ribozyme were initiated by adding 1.0 µL of 8 nM radiolabeled 36-mer, 12-mer, or 10-mer *P. carini*-specific substrates or the 38-mer Myotonic Dystrophy substrate. Reactions using the rP-8/4x-MD ribozyme were initiated by adding 1.0 µL of 8 nM radiolabeled 38-mer Myotonic Dystrophy-specific substrate or the 36-mer *P. carinii* substrate. The substrate sequences and how they base pair with the ribozymes are shown in FIG. 2. In each case the substrates were preincubated in the appropriate buffer (listed in the figures). After one hour, the reactions were terminated by adding an equal volume of stop buffer (10 M urea, 3 mM EDTA, and 0.1×TBE). The products and reactants were denatured for one minute at 90° C. and then separated on a 12% acrylamide/8 M urea gel. The gel was transferred to chromatography paper (Whatman 3MM CHR) and dried under vacuum. The bands were visualized and quantified on a Molecular Dynamics Storm 860 Phosphorimager.

The observed rate constant, $k_{obs}$, for the first (5' cleavage) and second (exon ligation) step of each reaction was quantified (Testa, S. M., Gryaznov, S. M. & Turner, D. H. (1998)

*Biochemistry* 37, 9379–9385; Mahadevan, M., Tsilfidis, C., Sabourin, L., Shutler, G., Amemiya, C., Jansen, G., Neville, C., Narang, M., Barcelo, J., O'Hoy, K., et al (1992) *Science* 255, 1253–1255). The first step was obtained from a plot of the percent intermediate plus percent product formed versus time, and the second step was obtained from a plot of percent product formed versus time. These observed rate constants reflect the rate of chemistry and any requisite conformation changes that occur.

Sequencing the trans-excision-splicing products. Products obtained from the trans-excision-splicing reactions were gel purified and sequenced by partial nuclease digestion using T1 (Epicentre; Madison, Wis.), U2 (Research Unlimited; Wellington, New Zealand), and Cl-3 (Research Unlimited) RNA nucleases. T1 reactions used $1.0 \times 10^{-4}$ units T1 in 200 mM Tris-HCl (pH 7.5), Cl-3 reactions used 0.33 units Cl-3 in 200 mM Tris-HCl (pH 7.5), and U2 reactions used 0.33 units U2 in 200 mM Tris-HCl (pH 3.5). Sequencing reactions utilized approximately 50 fmol of RNA and were incubated for 10 minutes at 55° C. Immediately after adding an equal volume of stop buffer to each reaction, aliquots were loaded on a 13.5% polyacrylamide/8 M urea gel. In parallel with the above reactions, we enzymatically sequenced chemically synthesized versions of the expected trans-excision-splicing products for comparison.

To determine if the 3' product of the first reaction step (5' cleavage) (FIG. 1B) is dissociating and then rebinding the same (or different) ribozyme before the second reaction step (exon ligation), TES reactions were conducted for one hour in 7 mM $MgCl_2$, 166 nM rP-8/4x ribozyme, 1.33 nM radiolabeled 36-mer substrate, and either 66.5 nM (50×) or 665 nM (500×) 3' exon mimic competitor r(GUGCUCU) (SEQ ID NO:16). The values reported are the average of six independent assays. Likewise, to determine if the 5' product of the first reaction step (5' cleavage) (FIG. 1B) is dissociating and then rebinding the ribozyme before the second step (exon ligation), TES reactions were conducted for one hr in 7 mM $MgCl_2$, 166 nM rP-8/4x ribozyme, 1.33 nM 36-mer non-radiolabeled substrate, and 1.33 nM radiolabeled 5' exon mimic competitor r(AUGACU) (SEQ ID NO:15). In each case the competitors were added simultaneously with the substrates.

EXAMPLE 2

Figure 3A:
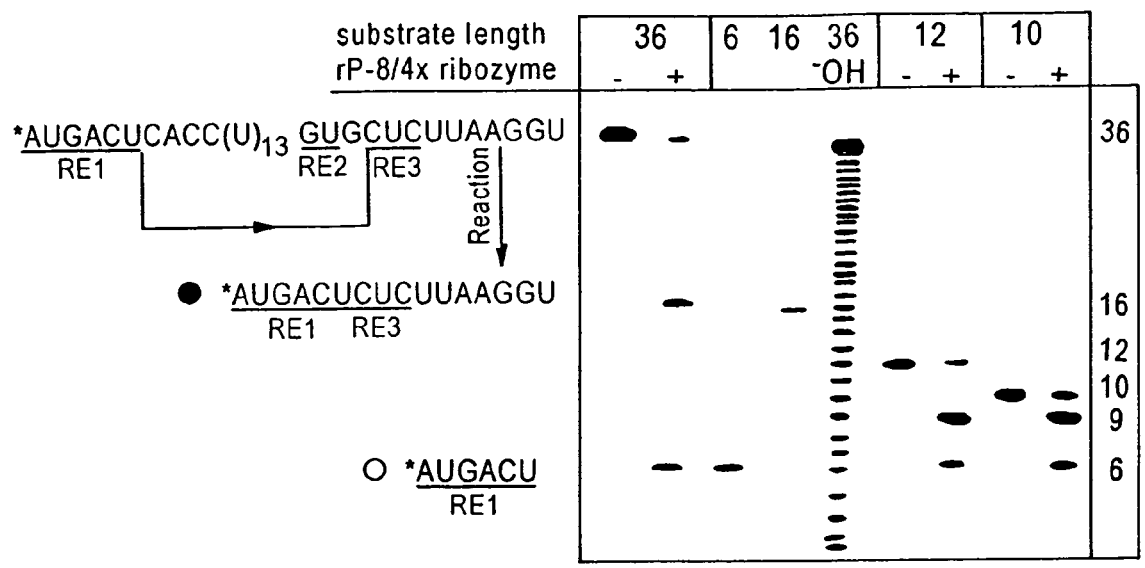
FIG. 3. The Trans-Excision-Splicing Reaction using the P. carinii system. The Trans-Excision-Splicing (TES) Reaction Using the P. carinii System. A) Polyacrylamide gel showing substrates and products of the TES reaction using 166 nM rP-8/4x ribozyme and 1.33 nM substrate at 7 mM $MgCl_2$ (36-mer) and 10 mM $MgCl_2$ (10-mer and 12-mer) at 44° C. The reaction using the 36-mer substrate is diagrammed on the left (SEQ ID NO: 10. SEQ ID NO:14, and SEQ ID NO:15). The regions of the substrate that bind to the ribozyme's recognition elements (labeled RE1 (SEQ ID NO:15). RE2, and RE3) are underlined. All reactions in the presence (+) and absence (−) of the rP-8/4x ribozyme were subjected to the same incubation conditions. TES reactions were conducted using a 36-mer substrate (to give a 16-mer product), a 12-mer substrate (9-mer product), and a 10-mer substrate (9-mer product). See FIG. 2 for the sequence of these substrates. The 6-mer lane shows a synthetic control for the 5' cleavage products, the 16-mer lane shows a synthetic control for the 16-mer TES product, and the $^-OH$ lane shows an alkaline digest of the 36-mer starting material. B). Graphs of TES reactions using the 36-mer substrate. All reactions were run as above except for the changing variable. The TES product is represented by filled circles and the 5' cleavage product by open circles. C). Graphs of TES reactions using the 10-mer substrate. All reactions were run as above except for the changing variable. The TES product is represented by filled triangles and the 5' cleavage product by open triangles. Each graph shows the average of two independent assays.

The *P. carinii* group I intron ribozyme catalyzes the trans-excision-splicing reaction. In order to test whether a ribozyme derived from a group I intron, and specifically one from *P. carinii*, catalyzes the trans-excision-splicing reaction, a substrate was designed that would bind the rP-8/4x ribozyme's native recognition element sequences (RE1, RE2, and RE3 in FIG. 1*b*). These substrate sequences were connected with a bridge consisting of the first four bases of the intron and 13 uridines (FIG. 2A). Uridines where chosen because of their relatively poor ability to form self-structures and the number of uridines (13) was chosen arbitrarily. Typical results at the optimized $MgCl_2$ concentration (7 mM) and the temperature (44° C.) are shown in FIG. 3A.

Figure 4:
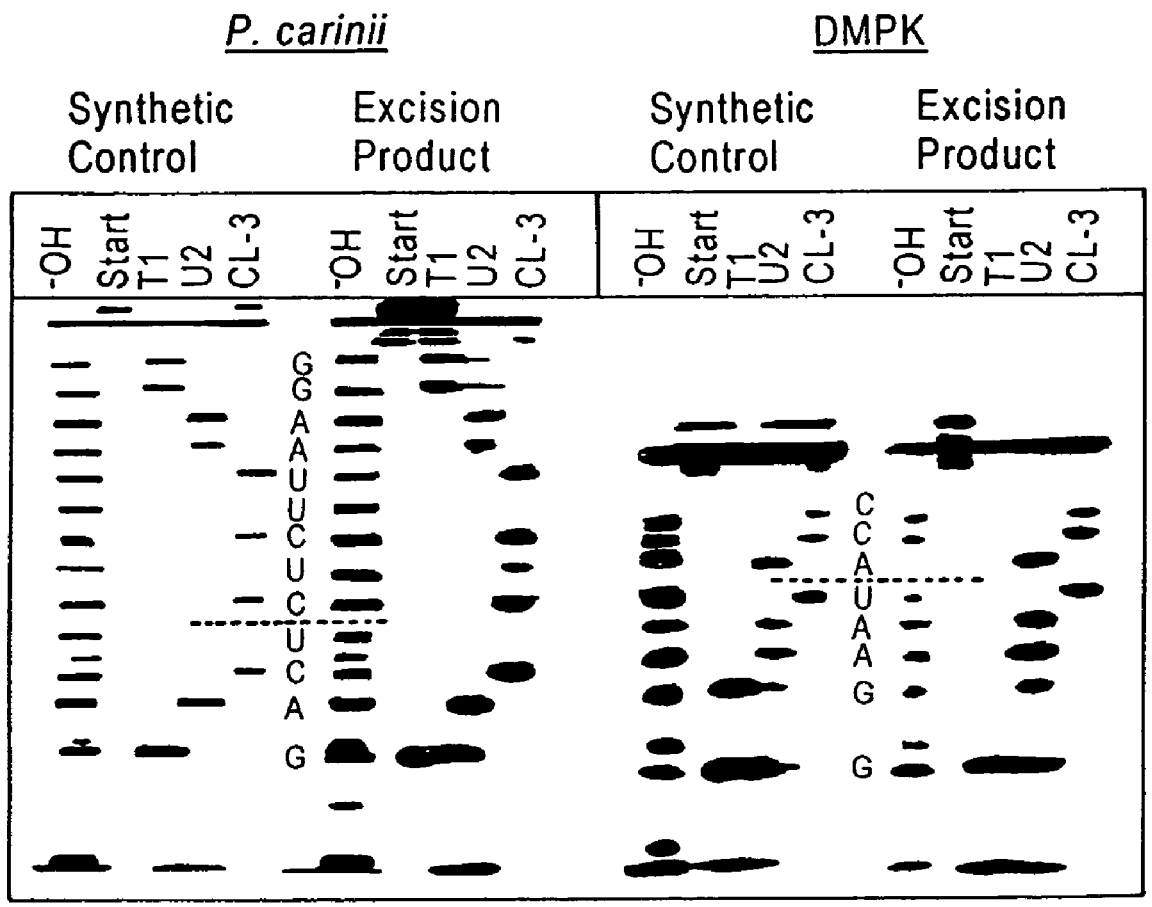
FIG. 4. Sequencing of Trans-Excision-Splicing Products. For each system, a chemically synthesized version of the expected product was sequenced and run adjacent to the isolated excision product. Left: the P. carinii 16-mer product that results from treating the 36-mer substrate with the rP-8/4x ribozyme. Right: the Myotonic Dystrophy 10-mer product that results from treating the 38-mer substrate with the rP-8/4x-MD ribozyme. The dotted line represents the newly created splice junction between the 5' and 3' ends of the substrate. Nuclease T1 is specific for guanosine, U2 for adenosine, and CL-3 primarily for cytidine. The $^-OH$ lane shows an alkaline digest of the starting material, and the lanes labeled 'Start' show the starting material.

The expected product band at 16 nucleotides in length was obtained in a yield of 25%±5% (for 6 independently run assays). This band was extracted from the gel matrix, repurified, and subjected to enzymatic sequencing, along with a chemically synthesized version of the expected product. The sequence and banding patterns were identical (FIG. 4), indicating that the expected trans-excision-splicing product was generating. The reaction also produced a band at six nucleotides. This is a product of the first step of the two-step trans-excision-splicing reaction (5' cleavage), and indicates that a portion of the transcript undergoes only the first step of the reaction. Also produced is a small amount of ribozyme mediated 3' splice site hydrolysis product at 26 nucleotides. Nonetheless, the rP-8/4x ribozyme contains the ability to bind a substrate in trans and catalyze the excision-splicing reaction.

Figure 3B:
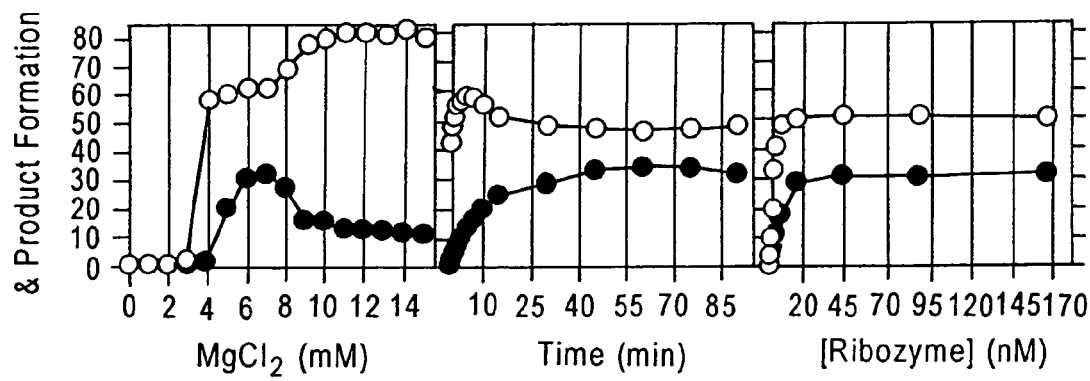

Apparently, a majority of the 36-mer substrate undergoes only the first step of the reaction. The dependence of the TES reaction on $MgCl_2$ concentration, time, and rP-8/4x concentration is shown in FIG. 3B. The $k_{obs}$ for the first and second step of the reaction are 1.69 and 0.05 $min^{-1}$, respectively. The reaction is complete after 40 minutes and only requires 20 nM ribozyme for maximal activity (with 1.33 nM substrate). These results show that the rP-8/4x ribozyme, in the absence of a nucleotide cofactor, inherently contains the ability to bind a substrate in trans and catalyze the TES reaction.

Even though there are 18 other uridines that could be sites of 5' cleavage and four other guanosines that could be sites of 3' splicing for the 36-mer substrate, only the expected TES product is generated. Apparently, the ribozyme recognition elements that define the individual catalytic steps are sequence specific. That the ribozyme can catalyze this reaction at all is surprising in that the relatively long bridging region could be expected to sterically hinder the binding of the substrate to the catalytic core of the ribozyme, or at least significantly hinder the required conformational rearrangement between the two catalytic steps. One or both of these might account for the majority (>50%) of the 36-mer substrate only undergoing the first catalytic step, in contrast to less than 10% only undergoing the first step for the self-splicing reaction in vitro (15, 17). The lack of product breakdown seen in the time dependence studies, however, indicates that the TES products themselves are not substrates for further reactions, although guanosine dependent 5' cleavage or ribozyme-mediated hydrolysis of the products could be a factor in vivo.

Figure 5:
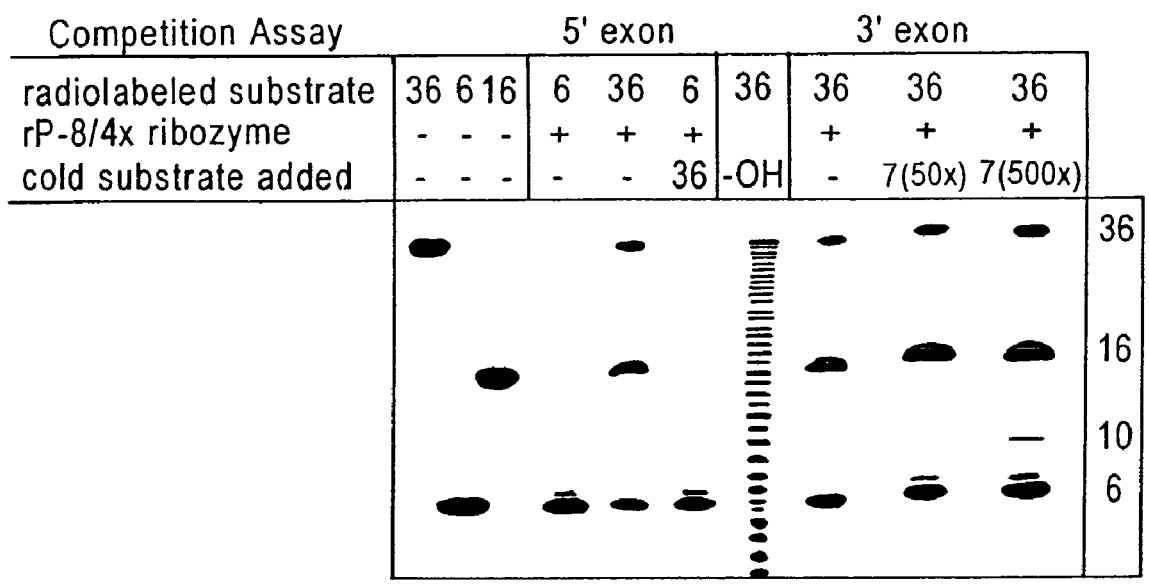
FIG. 5. Competition TES Reactions. Polyacrylamide gel showing substrates and products of TES reactions using 166 nM rP-8/4x, 7 mM $MgCl_2$, and 44° C. 'Radiolabeled substrate' refers to the length of the radiolabeled substrate at 1.33 nM final concentration and 'cold substrate' refers to the length of the non-radiolabeled substrate. The final concentrations of the cold substrates are 1.33 nM for the 36-mer, and 66.5 nM (50×) or 665 nM (500×) for the 7-mer, which is r(GUGCUCU) (SEQ ID NO:16). The two substrates for each reaction were added simultaneously. Lanes designated in the first box are length controls, the second box shows the 5' exon competition assay, the third box shows an alkaline digest of the 36-mer starting material, and the fourth box shows the 3' exon competition assay.

Previous studies utilizing the rP-8/4x ribozyme (Testa, S. M., Gryaznov, S. M. & Turner, D. H. (1998) *Biochemistry* 37, 9379–9385) show that the 5' exon mimic r(AUGACU) (SEQ ID NO:15) binds to the rP-8/4x ribozyme ($K_d$=5.2 nM at 37° C.) three orders of magnitude more tightly than the 3' exon mimic r(GUGCUCU) (SEQ ID NO:16) ($K_d$≈20 μM at 37° C.). Interestingly, maximum TES product formation occurs with as little as 20 nM ribozyme (at 44 ° C.), indicating that for final product formation the 5' and 3' exon intermediates produced during the 5' cleavage step might not dissociate and then rebind the ribozyme before the exon ligation step. To test for 5' exon dissociation and rebinding between the two steps, TES reactions were conducted with 166 nM rP-8/4x, 1.33 nM non-radiolableled 36-mer, and 1.33 nM radiolabeled 5' exon, r(AUGACU) (SEQ ID NO:15). In this case, if the 5' exon intermediate dissociates from the ribozyme, the radiolabeled 5' exon is just as likely to then bind the ribozyme and form the 16-mer product as the non-radiolabeled 5' exon intermediate. As seen in FIG. 5, no radiolabeled TES products are observed, indicating the 5' exon intermediate does not dissociate from the ribozyme between the two steps (for those 5' exon intermediates that undergo the complete reaction).

Likewise, to test for 3' exon intermediate dissociation and rebinding between the two reaction steps, TES reactions were conducted with 166 nM rP-8/4x, 1.33 nM radiolabeled 36-mer, and a 50 (66.5 nM) or 500 (665 nM) fold excess of a non-radiolabeled 3' exon mimic competitor, r(GUGCUCU) (SEQ ID NO:16) which would form a 10-mer competition product. At equal molar concentrations if the 3' exon intermediate dissociates from the ribozyme, the 7-mer competitor is 2.5 times more likely to bind the ribozyme and be a substrate in the second reaction step than the 30-mer 3' exon intermediate (data not shown). The results (FIG. 5) show that a 500-fold excess of cold competitor over substrate does not significantly reduce the amount of 16-mer product formed (19.4%±2.3% versus 22.8%±3%, respectively). The small amount of 10-mer product that is observed at 500-fold excess competitor over substrate (but not 50-fold excess) is not actually competing with the TES reaction. In these cases, the ribozymes that have bound radiolabeled 5' exon regions, and for which the 3' exon region has dissociated, are binding and reacting with a small amount of the huge excess of 3' exon competitor. Therefore, the vast majority of substrates that undergo the complete TES reaction do not have 3' exon intermediate dissociation and rebinding occurring between the two steps of the reaction. Apparently, substrates that undergo only the first reaction step do so because of nearly irreversible 5' or 3' exon intermediate dissociation. It follows that since intermediates to the complete TES reaction do not dissociate from the ribozyme, the TES reaction is intramolecular with regard to substrate.

EXAMPLE 3

Figure 2B:
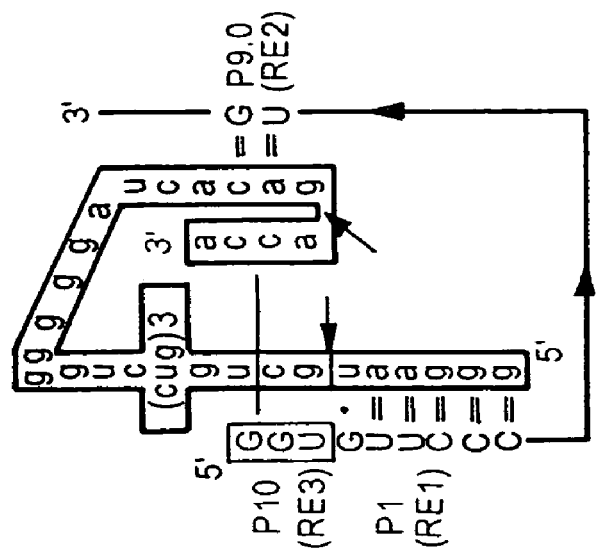
Figure 2B:
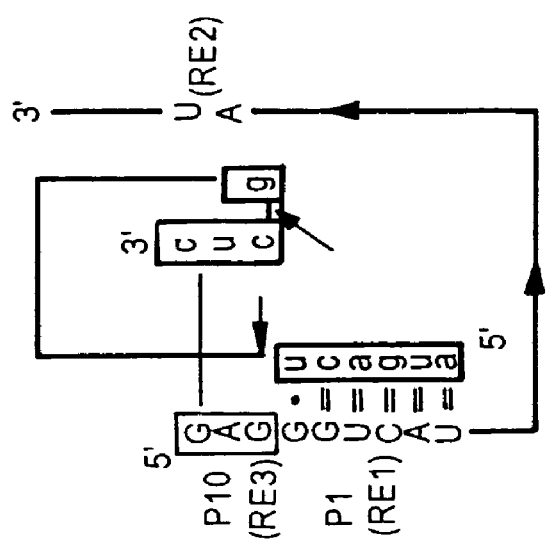
Figure 2B:
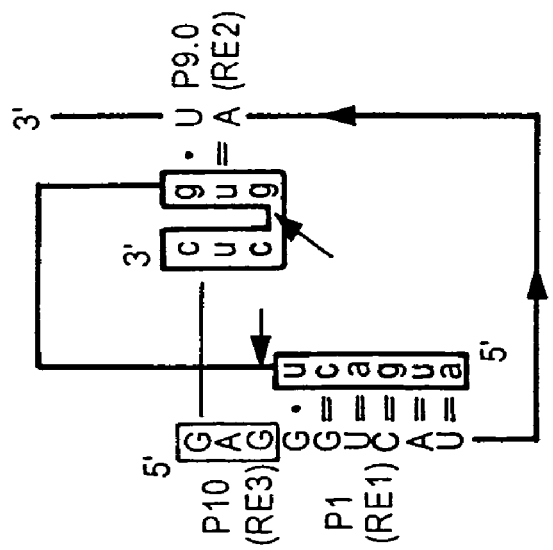
Figure 3C:
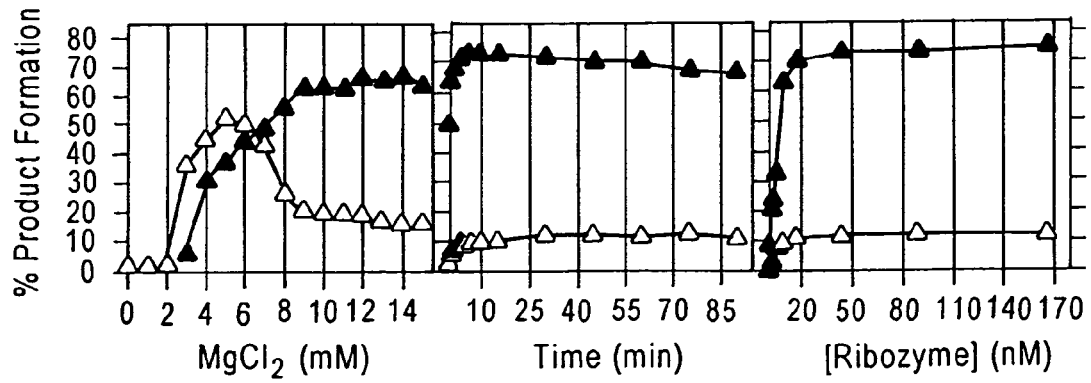

Excision of a single nucleotide using the *P. carinii*. ribozyme. In order to determine if a lower limit exists to the length of the excised region, we tested the TES reaction using the rP-8/4x ribozyme with two new substrates. One substrate is a 12-mer, r(AUGACUGUGCUC) (SEQ ID NO:7), and was designed to contain the minimum length bridging sequence that could utilize the 2 base pair RE2 interaction (to form the P9.0 helix) and the 3' guanosine thought to be required for self-splicing (FIG. 2Bi). The other substrate is a 10-mer, r(AUGACUGCUC) (SEQ ID NO:8), which can not utilize the RE2 interaction, and from which only one nucleotide would be excised (FIG. 2Bii). The results (FIG. 3A) show that, under the optimal conditions of 10 mM MgCl$_2$ and 44° C., both the 12-mer and 10-mer reactions lead to the formation of the expected 9-mer products, as confirmed by enzymatic sequencing (data not shown). The optimized reactions produce 72%±3.9% product for the 12-mer substrate and 69.3%±4.4% product for the 10-mer substrate (for 6 independently run assays). Thus, the rP-8/4x ribozyme can excise as little as a single nucleotide. The same approximate yield is obtained using the 12-mer and 10-mer substrates which suggests that the role of forming the P9.0 helix is not large in this case. Therefore, the RE2 interaction, although perhaps beneficial, is not required for sequence specific TES reactions. In addition, the 12-mer and 10-mer substrates lead to more than twice the product as compared with the 36-mer substrate, implicating the longer bridging region (which includes the four 5' bases of the intron) as being detrimental for this reaction. As the amount of substrate that undergoes at least the first reaction step is similar for all of the different substrates, 3' exon intermediate dissociation for the 36-mer likely accounts for the difference in extent of final product formation. The dependence of the 10-mer substrate reaction on MgCl$_2$ concentration, time, and rP-8/4x concentration is shown in FIG. 3C. The k$_{obs}$ for the first and second step of the reaction are 4.12 and 2.89 min$^{-1}$, respectively. In contrast to that for the 36-mer, the reaction with the 10-mer substrate is more favorable at MgCl$_2$ concentrations greater than 7 mM, and the second reaction step occurs approximately 50-fold faster. The origin of this effect is unknown, but could be due to the reduced steric hindrance of the smaller bridge on the required conformational rearrangement between the two reaction steps. This could reflect an increased affinity or accessibility of the 3' guanosine of the bridge for the G-binding site of the ribozyme. Indeed, previous reports suggest that the ability of the G-binding site to bind this endogenous guanosine drives the second step of the reaction (Mahadevan, M., Tsilfidis, C., Sabourin, L., Shutler, G., Amemiya, C., Jansen, G., Neville, C., Narang, M., Barcelo, J., O'Hoy, K., et al (1992) *Science* 255, 1253–1255; Harley, H. G., Rundle, S. A., MacMillan, J. C., Myring, J., Brook, J. D., Crow, S., Reardon, W., Fenton, I., Shaw, D. J., & Harper, P. S. (1993) *Am. J. Hum. Genet.* 52, 1164–1174).

EXAMPLE 4

Figure 6A:
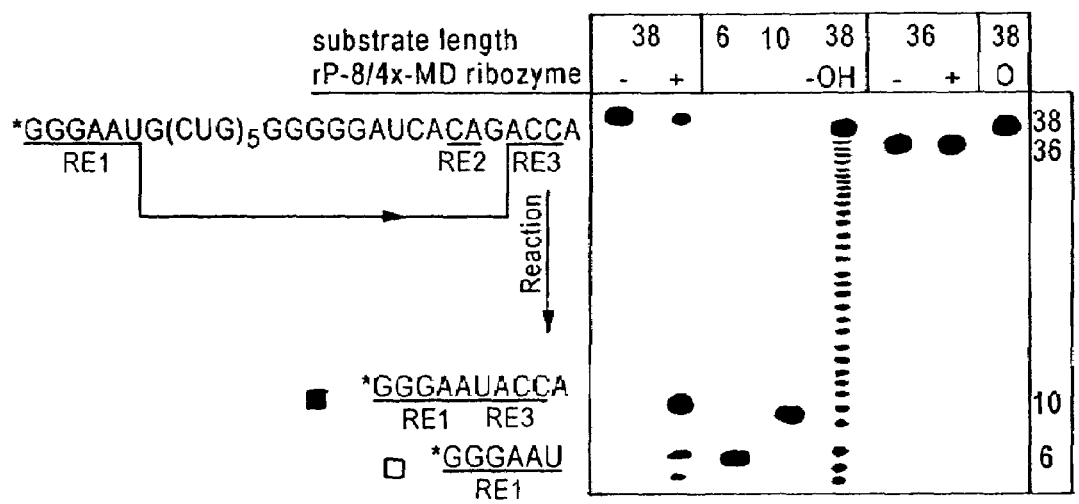
FIG. 6. The TES Reaction Using the DMPK Model System. A) Polyacrylamide gel showing substrates and products of the TES reaction using 166 nM rP-8/4x-MD ribozyme, 1.33 nM substrate, 13 mM MgCl$_2$, and 44° C. The reaction using the 38-mer DMPK mimic is diagrammed on the left (SEQ ID NO: 12. SEQ ID NO:17 and SEQ ID NO:18). The regions of the substrate that bind to the ribozyme's recognition elements are labeled RE1 (SEQ ID NO:18), RE2, and RE3. All reactions in the presence (+) and absence (−) of the rP-8/4x-MD ribozyme were subjected to the same incubation conditions. TES reactions were conducted using the 38-mer substrate (to give a 10-mer product). The 6-mer lane shows a synthetic control for the 5' cleavage products, the 10-mer lane shows a synthetic control for the 10-mer TES product, and the ⁻OH lane shows an alkaline digest of the 38-mer starting material. The lanes labeled 36 are TES reactions using the rP-8/4x-MD ribozyme with the 36-mer P. carinii substrate (at 13 mM MgCl$_2$), and the lane labeled 38 (lane o) is a reaction using the rP-8/4x ribozyme with the 38-mer DMPK mimic (at 7 mM MgCl$_2$). In these cases, no reaction occurs. B). Graphs of TES reactions using the 38-mer substrate and rP-8/4x-MD. All reactions were run as above except for the changing variable. The TES product is represented by filled squares and the 5' cleavage product by open squares.
Figure 6B:
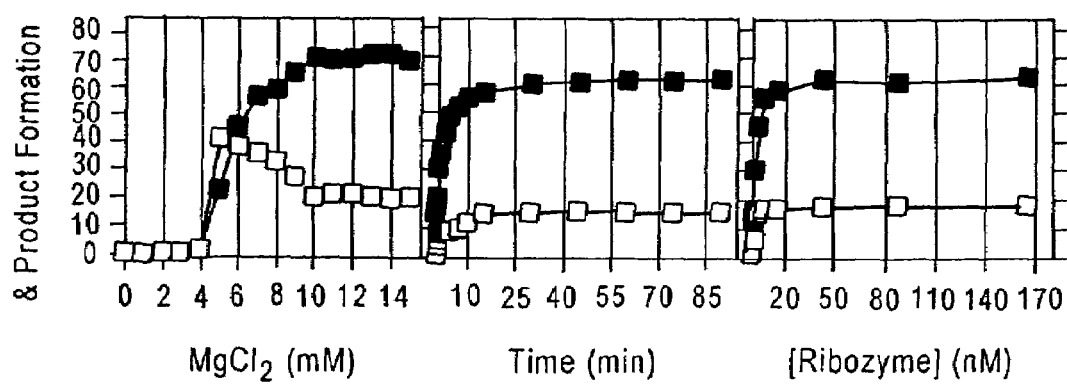

The sequence specificity of the *P. carinii* ribozyme can be altered. For the TES reaction to be useful, the recognition elements must be mutable in order to target predetermined sequences. Therefore, a truncated DMPK mimic model system was developed (FIG. 2Biii) for analyzing the ability of a re-engineered ribozyme to excise the RNA triplet repeat region whose expansion is the causative agent of the effects of the genetic disease, Myotonic Dystrophy. A ribozyme was designed to target the uridine immediately upstream of the repeats. Because there are five successive guanosines immediately following the repeats (which could lead to a mixture of TES products), the first guanosine downstream from the five successive guanosines was targeted. The substrate bridge contained 5 CUG repeats, as this is the smallest number of repeats thought to form the hairpin structure similar to that seen with the expanded transcripts. Myotonic Dystrophy patients actually have greater than 15 CUG repeats. Nevertheless, the ribozyme targets the flanking regions and would be the same regardless of the number of triplet repeats. This ribozyme is referred to as the rP-8/4x-MD ribozyme and this substrate the 38-mer DMPK mimic. The results at the optimum MgCl$_2$ concentration (13 mM) and temperature (44° C.) are shown in FIG. 6A. A 10 nucleotide product was obtained, as expected, in a yield of 61.1%±4.6% (for 6 independently run assays). Besides unreacted 6-mer generated from the first step of the reaction, no other products are produced to any significant amount, indicating a reasonably specific reaction. The 10-mer product was extracted from the gel and enzymatically sequenced, along with a chemically synthesized version of the expected product. The sequence and banding patterns obtained (FIG. 4) show that the expected TES product is being generated. Apparently, the ribozyme can be modified (at RE1, RE2, and RE3) to target non-native substrates. The dependence of this reaction on MgCl$_2$ concentration, time, and rP-8/4x-MD concentration is shown in FIG. 6B. The k$_{obs}$ for the first and second step of the reaction are 0.41 and 0.44 min$^{-1}$, respectively (note that these values are within experimental error and the rate of the second step is likely limited by the rate of the first step). Interestingly, the excision of this 28-mer bridge, which could include a triplet repeat hairpin structure, is substantially more effective than the 36-mer rP-8/4x system, which excises a 20-mer unstructured bridge. Thus, targets with large bridge regions are not necessarily poor reaction substrates.

To determine whether each ribozyme has specificity for its intended target, TES reactions were run using the rP-8/4x-MD ribozyme with the 36-mer *P. carinii* substrate at 13 mM MgCl$_2$, and the rP-8/4x ribozyme with the 38-mer DMPK mimic at 7 mM MgCl$_2$, each at 44° C. (FIG. 6A). In addition, the reaction was run using the rP-8/4x-MD ribozyme at 7 mM MgCl$_2$ and another reaction using the rP-8/4x ribozyme was run at at 13 mM MgCl$_2$ (data not shown). In these reactions, not even 5' cleavage products are observed, indicating that the ribozymes have some specificity for their intended target substrates. Although the MgCl$_2$ concentration required for maximum activity differs for all the reactions, they all occur at or below that required (15 mM) for maximum activity for the *P. carinii* group I intron self-splicing reaction in vitro. While it was known that the sequence of RE1 could be modified in reactions mimicking the first step of the self-splicing reaction (14, 20, 21), it was previously not known that all three recognition elements are modifiable. That these recognition elements completely specify binding and reactivity indicates that they are the primary determinants of specificity between the ribozyme and its substrate. In addition, bridging regions of different sequences and lengths (1, 3, 20, and 28 nucleotides) have been excised, indicating that perhaps a 3' G in the bridging region might be the only sequence requirement for the excised segment.

What is claimed is:

1. A modified trans-excision-splicing Group I ribozyme comprising at least two modifiable recognition elements, wherein at least one of said recognition elements is complementary to non-native target RNA sequence within a substrate having a 5' and 3' end and at least one of said recognition elements stabilizes binding of the ribozyme to a trans-excision splicing (TES) reaction intermediate product, and wherein the ribozyme initiates a first catalytic step in the absence of a guanosine cofactor and catalyzes a sequence specific excision of the non-native target RNA sequence, thereby forming a first intermediate comprising the 5' end of the substrate and a second intermediate comprising the 3' end of the substrate, each intermediate having a 5' and 3' end, and splices the 3' end of the first intermediate to the guanosine of the 5' end of the second intermediate created by the excision.

2. The ribozyme of claim 1 wherein the non-native target sequence is a single nucleotide.

3. The ribozyme of claim 1 wherein the non-native sequence comprises a premature stop codon.

4. The ribozyme of claim 1 wherein the non-native sequence comprises a frameshift mutation.

5. The ribozyme of claim 1 wherein the at least one recognition element is complementary to the triplet expansion associated with Muscular Dystrophy.

6. The ribozyme of claim 5 wherein the ribozyme removes the triplet expansion region involved in Muscular Dystrophy.

7. The ribozyme of claim 1 wherein the ribozyme is a modified *P. carinii* ribozyme.

8. An expression cassette comprising a promoter operably-linked to a nucleotide sequence encoding a trans-excision-splicing Group 1 ribozyme comprising at least two modifiable recognition elements, wherein at least one of said recognition elements is complementary to non-native target RNA sequence within a substrate and at least one of said recognition elements stabilizes binding of the ribozyme to a trans-excision splicing (TES) reaction intermediate product, and wherein the ribozyme initiates a first catalytic step in the absence of a guanosine cofactor and catalyzes a sequence specific excision of the non-native target RNA sequence, thereby forming a first intermediate comprising the 5' end of the substrate and a second intermediate comprising the 3' end of the substrate, each intermediate having a 5' and 3' end and splices the 3' end of the first intermediate created by the excision to the guanosine of the 5' end of the second intermediate created by the excision.

* * * * *

SEQUENCE LISTING

<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (13)..(18)
<223> OTHER INFORMATION: Represent altered recognition elements as
      compared to P-8/4x

<400> SEQUENCE: 1
cacgccgctt tcgggaacct ctatagtgag tcg                                  33

<210> SEQ ID NO 2
<211> LENGTH: 33
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (15)..(21)
<223> OTHER INFORMATION: Represent altered recognition elements as
      compared to P-8/4x

<400> SEQUENCE: 2
cgactcacta tagaggttcc cgaaagcggc gtg                                  33

<210> SEQ ID NO 3
<211> LENGTH: 25
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (11)..(12)
<223> OTHER INFORMATION: Represent altered recognition elements as
      compared to P-8/4x

<400> SEQUENCE: 3
ggtatagtct tgcctctttc gaaag                                           25

<210> SEQ ID NO 4
<211> LENGTH: 25
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature

```
<222> LOCATION: (14)..(15)
<223> OTHER INFORMATION: Represent altered recognition elements as
      compared to P-8/4x

<400> SEQUENCE: 4
ctttcgaaag aggcaagact atacc                                           25

<210> SEQ ID NO 5
<211> LENGTH: 30
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (13)..(15)
<223> OTHER INFORMATION: Represent altered recognition elements as
      compared to P-8/4x

<400> SEQUENCE: 5
cgactcacta taggtgttcc cgaaagcggc                                      30

<210> SEQ ID NO 6
<211> LENGTH: 30
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (16)..(18)
<223> OTHER INFORMATION: Represent altered recognition elements as
      compared to P-8/4x

<400> SEQUENCE: 6
gccgctttcg ggaacaccta tagtgagtcg                                      30

<210> SEQ ID NO 7
<211> LENGTH: 12
<212> TYPE: RNA
<213> ORGANISM: Artificial Sequence
<220> FEATURE:
<223> OTHER INFORMATION: Chemically synthesized

<400> SEQUENCE: 7
augacugugc uc                                                         12

<210> SEQ ID NO 8
<211> LENGTH: 10
<212> TYPE: RNA
<213> ORGANISM: Artificial Sequence
<220> FEATURE:
<223> OTHER INFORMATION: Chenically synthesized

<400> SEQUENCE: 8
augacugcuc                                                            10
```